US010690635B2

(12) United States Patent
Stadelmaier et al.

(10) Patent No.: US 10,690,635 B2
(45) Date of Patent: Jun. 23, 2020

(54) PURIFICATION OF GLUCAGON-LIKE PEPTIDE 1 ANALOGS

(71) Applicant: BACHEM HOLDING AG, Bubendorf (CH)

(72) Inventors: Andreas Stadelmaier, Muellheim (DE); Ralph O. Schoenleber, Lupsingen (CH); Daniel Samson, Basel (CH); Frank Dettner, Bubendorf (CH)

(73) Assignee: BACHEM HOLDING AG, Bubendorf (CH)

( * ) Notice: Subject to any disclaimer, the term of this patent is extended or adjusted under 35 U.S.C. 154(b) by 60 days.

(21) Appl. No.: 16/086,470

(22) PCT Filed: Mar. 21, 2017

(86) PCT No.: PCT/EP2017/056668
§ 371 (c)(1),
(2) Date: Sep. 19, 2018

(87) PCT Pub. No.: WO2017/162653
PCT Pub. Date: Sep. 28, 2017

(65) Prior Publication Data
US 2019/0113483 A1  Apr. 18, 2019

(30) Foreign Application Priority Data
Mar. 23, 2016 (EP) .................... 16162066

(51) Int. Cl.
*G01N 30/02* (2006.01)
*C07K 14/605* (2006.01)
*B01D 15/32* (2006.01)
*B01D 15/18* (2006.01)
*C07K 2/00* (2006.01)
*C07K 14/47* (2006.01)
*B01D 15/34* (2006.01)
*G01N 30/00* (2006.01)
*G01N 30/06* (2006.01)

(52) U.S. Cl.
CPC ......... *G01N 30/02* (2013.01); *B01D 15/1864* (2013.01); *B01D 15/325* (2013.01); *C07K 2/00* (2013.01); *C07K 14/4705* (2013.01); *C07K 14/605* (2013.01); *B01D 15/34* (2013.01); *G01N 2030/0065* (2013.01); *G01N 2030/027* (2013.01); *G01N 2030/065* (2013.01)

(58) Field of Classification Search
CPC ............. G01N 30/02; G01N 2030/065; G01N 2030/027; G01N 2030/0065; B01D 15/1864; B01D 15/325; B01D 15/34; C07K 14/4705; C07K 2/00; C07K 14/605
See application file for complete search history.

(56) References Cited

U.S. PATENT DOCUMENTS

2006/0211616 A1* 9/2006 Staby .................. C07K 14/605
514/6.8

FOREIGN PATENT DOCUMENTS

| CN | 103275208 A | 9/2013 |
|---|---|---|
| EP | 0 708 179 A2 | 4/1996 |
| EP | 1 664 109 B1 | 7/2009 |
| EP | 2 813 514 A1 | 12/2014 |
| WO | 98/08871 A1 | 3/1998 |
| WO | 00/55184 A1 | 9/2000 |
| WO | 00/55203 A1 | 9/2000 |
| WO | 2005/019261 A1 | 3/2005 |
| WO | 2005/019262 A1 | 3/2005 |
| WO | 2010/066734 A1 | 6/2010 |
| WO | 2011/107447 A1 | 9/2011 |
| WO | 2011/161007 A1 | 12/2011 |
| WO | 2014/199397 A2 | 12/2014 |
| WO | 2016/005960 A1 | 1/2016 |

OTHER PUBLICATIONS

International Preliminary Report on Patentability in International Application No. PCT/EP2017/056668, dated Oct. 4, 2018.
Beaven et al., "Formation and Structure of Gels and Fibrils from Glucagon," European J. Biochem. 11:37-42 (1969).
Wang et al., "Transformation of Oligomers of Lipidated Peptide Induced by Change in pH." Molecular Pharmaceutics 12:411-419 (2015).
Wajcberg et al, "Liraglutide in the management of type 2 diabetes," Drug Design, Development and Therapy 4:279-290 (2010).
Written Opinion of the International Searching Authority for PCT/EP2017/056668, dated Sep. 28, 2017.

\* cited by examiner

*Primary Examiner* — Sudhakar Katakam
(74) *Attorney, Agent, or Firm* — J.A. Lindeman & Co. PLLC

(57) ABSTRACT

The present invention refers to a method of purifying a glucagon-like peptide 1 analogs, the method comprising a two dimensional reversed phase high performance liquid chromatography protocol, wherein the first step is carried out at a pH value between 7.0 to 7.8 using a mobile phase comprising a phosphate buffer and acetonitrile, and the second step is carried out at a pH value below 3.0 using a mobile phase comprising trifluoroacetic acid and acetonitrile.

20 Claims, 3 Drawing Sheets

Specification includes a Sequence Listing.

Fig. 1

| | | |
|---|---|---|
| Glucagon | HSQGTFTSDYSKYLDSRRAQDFVQWLMN | (SEQ ID NO:1) |
| GLP-2 | HADGSFSDEMNTILDNLAARDFINWLIQTKITD | (SEQ ID NO:2) |
| GLP-1(7-37) | HAEGTFTSDVSSYLEGQAAKEFIAWLVKGRG | (SEQ ID NO:3) |
| Liraglutide | HAEGTFTSDVSSYLEGQAAKEFIAWLVRGRG | (SEQ ID NO:4) |
| Exendin 4 (1-39) | HGEGTFTSDLSKQMEEEAVRLFIEWLKNGGPSSGAPPPS-NH$_2$ | (SEQ ID NO:5) |
| Exenatide | HGEGTFTSDLSKQMEEEAVRLFIEWLKNGGPSSGAPPPS-NH$_2$ | (SEQ ID NO:6) |
| Lixisenatide | HGEGTFTSDLSKQMEEEAVRLFIEWLKNGGPSSGAPPSKKKKKK-NH$_2$ | (SEQ ID NO:7) |

PURIFICATION OF GLUCAGON-LIKE PEPTIDE 1 ANALOGS

The present invention generally relates to the field of peptide purification at an industrial or laboratory scale. The present invention is directed to methods of effectively purifying glucagon-like peptide 1 analogs, such as Liraglutide.

In preferred embodiments, the present invention refers to a method of purifying glucagon-like peptide 1 analogs, the method comprising a two dimensional reversed phase high performance liquid chromatography protocol, wherein the first step is carried out at a pH value between 7.0 to 7.8 using a mobile phase comprising a phosphate buffer and acetonitrile, and the second step is carried out at a pH value below 3.0 using an aqueous mobile phase comprising trifluoroacetic acid and acetonitrile.

The human GCG gene (HGNC:4191) encodes multiple related peptides including glucagon, glucagon-like peptide 1 (GLP-1) and glucagon-like peptide 2 (GLP-2). These share considerable sequence homology (cf. FIG. 1) and are important in controlling blood glucose homeostasis, intestinal cell proliferation, and satiety. Abnormal GLP-1 function has been implicated in obesity, postprandial reactive hypoglycemia, and type 2 diabetes. Hence, GLP-1 analogs are of considerable interest in pharmaceutical research. Variants and derivatives of the peptide hormon exendin-4 found in the Gila Monster (Heloderma suspectum) as well as variants and derivatives of the GLP-1 peptide itself are being extensively studied. Marketed drugs comprise Exenatide and Lixisenatide, both derived from the exendin-4 peptide, as well as the GLP-1 derived Liraglutide.

Liraglutide (N-ε-(γ-Glu(N-α-hexadecanoyl)))-Lys$^{26}$Arg$^{34}$-GLP-1(7-37), also known as NN2211, has been approved for the treatment of type 2 diabetes and for the treatment of obesity in adults with related comorbidity.

The substance is being produced at an industrial scale by recombinant techniques. WO 1998/008871 describes reacting a recombinantly expressed parent peptide with Nα-hexadecanoyl-Glu(ONSu)-OtBu to obtain Liraglutide.

It is desirable to provide methods for the large scale, full chemical synthesis of glucagon-like peptides such as Liraglutide. Chemical peptide synthesis has been extensively described in the literature. Two standard approaches to chemical peptide synthesis can be distinguished, namely liquid phase peptide synthesis (LPPS) and solid phase peptide synthesis (SPPS). Moreover, hybrid approaches can be utilized, where fragments are first synthesized by one of the above techniques and then joined together using the other. LPPS, also referred to as solution peptide synthesis, takes place in a homogenous reaction medium. Successive couplings yield the desired peptide. In SPPS, a peptide anchored by its C-terminus to an insoluble polymer resin is assembled by the successive addition of the protected amino acids constituting its sequence. Because the growing chain is bound to the insoluble support, the excess of reagents and soluble by-products can be removed by simple filtration. However, in particular for the synthesis of large peptides, resin-bound side products can accumulate in addition to side products formed during deprotection or due to degradation. As a result, the purification of the final product may very challenging.

Purification of glucagon-like peptides is particularly demanding due to their propensity to aggregate. It is known that glucagon and glucagon-like peptides tend to aggregate at acidic pH (e.g. European J. Biochem. 11 (1969) 37-42). The present invention provides methods for the production and purification of GLP-1 and GLP-1 analogs, in particular for the purification of Liraglutide.

Patent application CN-A 103275208 discloses a purification protocol for Liraglutide comprising a reversed phase high performance chromatography (RP-HPLC) using a C18 column and acidic mobile phases consisting of 0.1% trifluoroacetic acid (TFA) solutions with acetonitrile or of 1% aqueous acetic acid solution with acetonitrile. The overall yield is designated as being only 20.2%.

WO 2011/161007 discloses a method for the purification of GLP-1 derivatives. The method involves a two dimensional RP-HPLC, wherein organic solvent in the mobile phase is acetonitrile and the second dimension is carried out using a basic buffer at a pH between 8.0 and 11.0. In preferred embodiments, a C18 column is used with ammonium phosphate/acetonitrile at a pH of 2.4 as mobile phase in the first dimension and ammonium acetate/acetonitrile or ammonium carbonate/acetonitrile at a pH of 9.5 as mobile phase in the second dimension. The maximal degree of purity reported is 97.4%. Therefore, the purity is not as high as desired and the peptide is obtained in a basic buffer which may have drawbacks for the storage of the peptide, in particular as the basic buffer agents used in WO 2011/161007 are not evaporable. The removal of the basic buffer agent may require additional desalting steps.

EP-A 2 813 514 discloses a method for the purification of Liraglutide. The method involves a three-dimensional RP-HPLC purification, with octylsilane bonded silica as a stationary phase and an aqueous isopropanol/TFA/acetonitrile system as a mobile phase in the first dimension; cyanosilane bonded silica as a stationary phase and an aqueous perchloric acid/acetonitrile system as a mobile phase in the second dimension; and octylsilane bonded silica as a stationary phase and an aqueous ammonia/acetonitrile system as a mobile phase in the third dimension. Although in a laborious procedure three subsequent HPLC purification steps using different solid phases and completely different mobile phases are employed, the maximal degree of purity reported is 98.7%.

WO 2014/199397 discloses purification of crude Liraglutide synthesized by a hybrid approach by means of RP-HPLC using a C8 column and a TFA/methanol/acetonitrile system as a mobile phase. The obtained composition comprises large amounts of toxic methanol. The resulting purity is reported as above 97%.

WO 2010/066734 discloses the use of counter current chromatography for the purification of peptides. Reversed phase and anion exchange columns are used as stationary phases. Herein, a method based on counter ions is described on a rather theoretic basis. This method is rather complex.

WO 2000/055203 and WO 2000/055184 disclose purification of peptides by ion exchange chromatography. Similarly, WO 2005/019261 discloses a method of separating Liraglutide from a racemic contaminant by ion exchange chromatography.

The compositions obtained from such methods comprise considerable amounts of salts which will often be higher than desired and then have to be removed in further purification steps.

WO 2011/107447 discloses purification of various peptides by RP-HPLC, wherein the pH of the mobile phase is kept within 1 unit of the isoelectric point of the peptide and elution is preferably effected by a pH gradient in acidic range.

EP-B 1 664 109 discloses purification of peptides by RP-HPLC, wherein the mobile phase comprises an alcohol and a buffer tightly controlling the pH value at a setpoint selected from the range of pH 4-10.

WO 2016/005960 discloses a two-step purification scheme for Liraglutide, which describes a first purification step using irregular C18 silica media—10 micron particle size and a mobile phase comprising 10 mM Tris at pH 8.0. The second step uses C18 RP-HPLC media of 5 micron particle size and a mobile phase comprising 0.1% TFA. Elution is effected by a step gradient of acetonitrile. The average purity of the pooled fractions is indicated as 97% and hence not as high as desired. Moreover, the use of two different stationary phases is not economical.

In spite of the large body of prior art, there is still a need for improved methods enabling the industrial production of highly pure glucagon-like peptide 1 analogs and derivatives.

Surprisingly, a simple method for the preparation of highly pure Liraglutide has been found. It has been found that employing two consecutive chromatographic steps of first using a first phosphate buffer containing mobile phase with a pH between 7.0 and 7.8 (7.0≤pH<7.8) and subsequently using a second TFA-containing mobile phase of acidic pH is advantageous. It was found that column clogging can be well avoided and that the same stationary phase can be used in both steps. In the experiments performed, reproducibly high yields and high purities of the pooled fractions above 98.8% (even above 99%) could be achieved.

In general, several abbreviations and definitions are used throughout the present invention:
ACN acetonitrile
AcOH acetic acid
Boc tert. butyloxycarbonyl
DTE 1,4-dithioerythriol
DTT 1,4-dithiothreitol
EDT 1,2-ethanedithiol
Fmoc 9-fluorenylmethyloxycarbonyl
GLP-1 glucagon-like peptide 1
GLP glucagon-like peptide
HPLC high performance liquid chromatography
The term HPLC as used herein includes UHPLC.
LC-MS Liquid chromatography-mass spectrometry
LPPS liquid phase peptide synthesis
NH$_4$OAc ammonium acetate
RP-HPLC reversed phase high performance liquid chromatography
SEC size exclusion chromatography
SPPS solid-phase peptide synthesis
tBu tert. Butyl
TEAP triethylammonium phosphate
TFA trifluoroacetic acid
TIPS triisopropylsilane
UHPLC ultra high performance liquid chromatography Unless otherwise stated, pH values are indicated for the temperature at which the respective aqueous solution is to be used.

Amino acids will be referred to interchangeably by either their full name (exemplified: alanine), 3-letter code according to WIPO Standard ST. 25 (e.g. Ala), or 1-letter code (e.g. A). As far as the enantiomeric form is not expressly specified, L-amino acids are in general referred to. It should be noted, however, that the present invention can likewise be put to practice using D-amino acids and other stereoisomers.

As used herein, the term "peptide" and "polypeptide" may be understood interchangeably. Unless indicated otherwise, peptide sequences are indicated herein starting with the N-terminus (left) and ending with the C-terminus (right).

Table 1 illustrates different notations, which are equivalent and will be used interchangeably throughout this document.

TABLE 1

Notation of peptides

| Notation | Explanation |
| --- | --- |
| H-Gly-Leu-Ala-Phe-OH | This notation stresses that the N-terminal amino group ("H") and C-terminal carboxyl ("OH") group are not modified. |
| Gly-Leu-Ala-Phe | Terminal groups are only expressly stated if they are modified. |
| GLAF | 1-letter code. Terminal groups are only expressly stated if they are modified. |
| Glycyl-L-leucyl-L-alanyl-L-phenylalanine | "written out in full" |

The following notation will be used for amino acid derivatives: Substituents at the alpha amino group (Nα) are indicated to the left of the amino acid symbol and separated by a hyphen, substituents at the alpha carboxy group are indicated to the right of the amino acid symbol and separated by a hyphen, substituents at the side chain are indicated in brackets immediately to the right of the amino acid symbol. For unmodified alpha-amino acids, the substituent at the alpha amino group (Nα) is a proton (H—) and the substituent at the alpha carboxy group is a hydroxyl (—OH)

For branched dipeptides, this notation is adhered to in a nested format. For example, Fmoc-Lys(Boc-Glu-OtBu)-OH refers to a Lys derivative with a Fmoc protected alpha amino group and a free alpha carboxyl group, whose side chain is substituted with a glutamyl moiety having a Boc protected alpha amino group and an OtBu protected carboxyl group. The glutamyl moiety forms an amide bond to the Lys side chain via its gamma carboxyl group.

The analogous notation is used for substituted amino acids, which are part of a peptide. For example, Aaa1-Aaa2-Lys(Boc-Glu-OtBu)-Aaa4-Aaa5 refers to a branched pentapeptide, where the Lys side chain at position 3 is substituted with a amide bonded glutamyl moiety having a Boc protected alpha amino group and an OtBu protected carboxyl group. Hence, said amide bond is between the Lys' epsilon amino group and the Glu's gamma carboxyl group.

The term "glucagon-like peptide" or GLP as used herein refers to the homologous peptides derived from the GCG gene (HGNC:4191), the exendins and analogs thereof as well as derivatives of any of the foregoing. FIG. 1 depicts a sequence alignment of prototypical glucagon-like peptides.

The terms "glucagon-like peptide 1 analogs" and "GLP-1 analogs" are used herein interchangeably. As used herein, they relate to peptides capable of binding to the GLP-1 receptor. Derivatives and analogs of GLP-1 (7-37) and of exendin 4 (1-39) such as Exenatide, Lixisenatide, and Liraglutide are preferred GLP-1 analogs. Exemplarily, a GLP-1 analog may comprise a polypeptide strand having at least 80% homology to SEQ ID NO:4, more preferably a polypeptide strand having at least 90% homology to SEQ ID NO:4, in particular a polypeptide strand having at least 95% homology to SEQ ID NO:4 and, optionally, also a modification at the lysine moieties homolog to Lys20 of SEQ ID NO:4. Homology as used herein is preferably sequence homology determined over the entire sequence of SEQ ID NO: 4. As used herein, sequence homology may refer to any definition of sequence homology known in the art. In particular, sequence homology may be understood as sequence homology determined by BLAST (Basic Local Alignment Search Tool) of the National Center for Biotechnology Information (NCBI) in the version of the filing date of the present application.

The term "analogs" or "analogs" as used herein is used for peptides whose sequence is derived from a first peptide sequence by replacement of up to 50% of the amino acid moieties, and/or by deletion of up to 10% of the amino acid moieties of said first peptide sequence, and/or by addition of up to 10 amino acid moieties. Preferred analogs are derived from a first peptide sequence by replacement of up to 20% of the amino acid moieties, and/or by deletion of up to 10% of the amino acid moieties of said first peptide sequence, and/or by addition of up to 10 amino acid moieties.

The term "derivative" or "derivatives" as used herein refers to a compound which can be obtained from a first compound by a chemical reaction. As a result, a derivative may differ from the first compound by the presence or absence of substituents. For example, amino acid derivatives for use in SPPS usually differ from the amino acid they are derived from at least by the presence of an amino protecting group.

The present invention is directed to methods for effectively purifying a GLP-1 analogue such as Liraglutide.

It will be understood by a person skilled in the art that a GLP-1 analogue as used herein may optionally bear any counter ions known in the art, such as anions or cations, such as e.g., chloride ions, acetate ions, carbonate ions, hydrocarbonate ions, sodium ions, potassium ions, magnesium ions, any ions of a cleavage solution (e.g., TFA ions, bromide ions, perchlorate ions, ammonium ions) and/or cations or anions of residuals of protecting groups. Further, a peptide may optionally be covalently or non-covalently associated to traces of one or more scavengers, such as, e.g., triisopropylsilane (TIS), dithiothreitol (DTT), anisole, thioanisole or 1,2-ethanedithiol.

While the following teachings are often in respect to Liraglutide, it should be understood that they are likewise applicable to any other GLP-1 analogue.

In particular, one aspect of the present invention relates to a method for the purification of Liraglutide, comprising the following steps a) through c):

a) Providing a liquid composition C comprising Liraglutide and at least one unwanted component;
b) Subjecting the composition C to a first reversed phase HPLC purification at a pH between 7.0 and 7.8, wherein a hydrocarbon bonded silica is used as a stationary phase, a mobile phase comprising an aqueous phosphate buffer AB1 and acetonitrile is used, and elution is effected by gradually increasing the acetonitrile concentration within the mobile phase while collecting Liraglutide containing fractions; and
c) Subjecting the pooled Liraglutide containing fractions obtained in step b) to a second reversed phase HPLC purification at a pH below 3.0, wherein a hydrocarbon bonded silica is used as a stationary phase, a mobile phase comprising trifluoroacetic acid and acetonitrile is used, and elution is effected by gradually increasing the acetonitrile concentration within the mobile phase while collecting fractions containing purified Liraglutide.

In one embodiment, the method of the present invention further comprises the step of d) Subjecting the Liraglutide obtained in step c) to a third reversed phase HPLC purification at a pH between 7.0 and 7.8, wherein a hydrocarbon bonded silica is used as a stationary phase, a mixture of an aqueous buffer AB2 with acetonitrile is used as a mobile phase, and elution is effected by gradually increasing the acetonitrile concentration within the mobile phase while collecting fractions containing purified Liraglutide.

The term "providing a liquid composition C comprising Liraglutide and at least one unwanted component" may be understood in the broadest sense as obtaining any liquid composition containing Liraglutide and at least one unwanted component. Liraglutide may be provided by any means known in the art. Exemplarily, it may be obtained from Solid Phase Peptide Synthesis (SPPS) or Liquid Phase Peptide Synthesis (LPPS) or a combination thereof. Alternatively, the plain polypeptide strand may also be obtained from a biotechnological method and the obtained polypeptide strand may be subsequently modified by chemical/synthetic means.

The term "unwanted component" is used herein in the broadest sense for any compound considered an impurity. Particularly preferred types of impurities are formed during synthesis and storage of Liraglutide and may exemplarily be selected from the group consisting of amino acids, peptides and derivatives thereof. In particular encompassed are impurities selected from the group consisting of amino acids, peptides, and derivatives thereof, which may result from processes such as premature chain termination during peptide synthesis, omission or unintended addition of at least one amino acid during peptide synthesis, incomplete removal of protecting groups, side reactions occurring during amino acid coupling or Fmoc deprotection steps, inter- or intramolecular condensation reactions, side reactions during peptide cleavage from a solid support, racemization, any other type of isomer formation, deamidation, (partial) hydrolysis, and aggregate formation. It is well known in the art that glucagon and glucagon-like peptides are prone to aggregate formation, and that low pH values often facilitate this process, i.e. that low pH values represent a destabilizing condition (cf., e.g., Wang et al., Mol. Pharm 12:411-419). Peptidic contaminations resulting from such processes as outlined above are sometimes referred to as "related substances".

In a particularly preferred embodiment, the unwanted component is a peptidic impurity. As used herein, the expression "peptidic impurity" refers to unwanted peptidic compounds and comprises in particular HMW impurities, derivatives of the peptide to be purified, truncated variants of the peptide to be purified, deletion variants of the peptide to be purified, and derivatives of such truncated and deletion variants. Peptidic impurities are routinely determined by suitable analytic chromatography methods including RP-UHPLC.

In one embodiment, the unwanted component comprises covalent or non-covalent aggregates of the peptide to be purified. Such unwanted components are physiologically inactive or of unknown physiological effect and have a molecular weight above 5000 Da. They are referred to herein as "high molecular weight (HMW) impurities". In another embodiment, the unwanted component is a derivative of the peptide to be purified, e.g. the result of oxidation or hydrolysis of amino acid side chains and/or a side product formed during peptide synthesis. In another embodiment, the unwanted component is a truncated variant of the peptide to be purified or a derivative of such a truncated variant. As used herein, the expression "truncated variant" refers to continuous fragments, i.e. subsequences without gaps, of a given peptide, which lack one or more amino acids at the N-terminus and/or the C-terminus of the peptide sequence. In another preferred embodiment, the unwanted component comprises deletion variants of the peptide to be purified or derivatives of such deletion variants. As used herein, the expression "deletion variant" is used to refer to variants of the peptide to be purified, which differ from it in that their primary sequence lacks a single or multiple amino acid(s). The "omitted" amino acid(s) may be at any position within the original peptide sequence. Hence, truncation variants can be considered a specific type of deletion variants.

In a particularly preferred embodiment, the peptide to be purified is Liraglutide. In a most preferred embodiment, the method according to the present invention allows to remove peptidic impurities so as to yield an essentially pure Liraglutide preparation. It was shown that the methods of the present invention yield essentially pure Liraglutide containing not more than 0.5% of any individual peptidic impurity, as assessed in terms of relative peak area observed by analytical chromatography, preferably with UV detection at a wavelength between 205 and 230 nm.

Liraglutide deletion variants may preferably be peptides consisting of 27-30 continuous amino acids, which differ from Liraglutide's molecular structure in that they are lacking up to four amino acids out of the primary sequence of the Liraglutide peptide backbone (SEQ ID NO:4), and which may optionally have additional alterations at 2-5 amino acid side chains or at the (N-ε-(γ-Glu(N-α-hexadecanoyl)))-substituent at the Lys moiety corresponding to Lys 20 of SEQ ID No:4.

In other words, Liraglutide deletion variants may be defined as peptides of 27 to 30 amino acid moieties in length, which share at least 80% homology with SEQ ID NO:4, calculated over the entire length of SEQ ID NO:4, and which optionally comprise a modification, e.g. a (N-ε-(γ-Glu(N-α-hexadecanoyl)))-substituent, at the lysine moiety homolog to $Lys^{20}$ of SEQ ID NO:4.

In some embodiments, the unwanted component comprises at least one species of $Trp(O)^{25}$-Liraglutide, and/or at least one species of $Trp(2O)^{25}$-Liraglutide and/or $Kyn^{25}$-Liraglutide and/or a Liraglutide deletion variant lacking $Gly^{31}$.

In the context of the present application, the expression "$Trp(O)^{25}$-Liraglutide" is used to designate a Liraglutide derivative, where the indole moiety in the side chain of Trp at position 25 is oxidized by incorporation of a single oxygen atom. The expression "$Trp(2O)^{25}$-Liraglutide" is used to designate a Liraglutide derivative, where the indole moiety in the side chain of Trp at position 25 is oxidized by incorporation of two oxygen atoms. Finally, the expression $Kyn^{25}$-Liraglutide is used for Liraglutide derivatives where kynurenine replaces Trp at position 25.

The embodiments of the invention described herein can advantageously be used to isolate Liraglutide from a crude preparation obtained after synthesis. Although the present invention is in no way limited to specific methods of Liraglutide synthesis, a preferred embodiment involves the purification of a chemically synthesized Liraglutide peptide. The Liraglutide peptide may be synthesized, e.g., by Fmoc solid-phase peptide synthesis using suitably protected amino acid and dipeptide derivatives.

Preferably, the composition C comprises Liraglutide or a salt thereof, which was prepared by a method comprising the following steps (i)-(iii):
(i) providing a solution S comprising a peptide of formula I:
  His-Ala-Glu-Gly-Thr-Phe-Thr-Ser-Asp-Val-Ser-Ser-Tyr-Leu-Glu-Gly-Gln-Ala-Ala-$B^1$-Glu-Phe-Ile-Ala-Trp-Leu-Val-Arg-Gly-Arg-Gly,
  wherein $B^1$ is Lys(palmitoyl-Glu-OH) or Lys(H-Glu-OH);
(ii) precipitation of the peptide of step (i) by means of mixing solution S with an anti-solvent comprising diisopropyl ether and acetonitrile, wherein the volume ratio (diisopropyl ether:acetonitrile) is in the range of from (3:1) to (10:1); and
(iii) isolating the precipitate obtained from step (ii), preferably by means of filtration and/or centrifugation.

More preferably, the whole amount of crude Liraglutide contained in the composition C is obtained by the above method.

In a particularly preferred aspect, the composition C comprises a crude Liraglutide or a salt thereof, which was prepared by a method comprising the following steps (i)-(iii):
(i) providing a solution S comprising a peptide of formula I:
  His-Ala-Glu-Gly-Thr-Phe-Thr-Ser-Asp-Val-Ser-Ser-Tyr-Leu-Glu-Gly-Gln-Ala-Ala-$B^1$-Glu-Phe-Ile-Ala-Trp-Leu-Val-Arg-Gly-Arg-Gly,
  wherein $B^1$ is Lys(palmitoyl-Glu-OH) or Lys(H-Glu-OH);
  wherein the provision of said solution S comprises:
  (i-a) providing a precursor peptide conjugated to a solid phase:
    His-Ala-Glu-Gly-Thr-Phe-Thr-Ser-Asp-Val-Ser-Ser-Tyr-Leu-Glu-Gly-Gln-Ala-Ala-$B^2$-Glu-Phe-Ile-Ala-Trp-Leu-Val-Arg-Gly-Arg-Gly-[resin],
    wherein $B^2$ is Lys(palmitoyl-Glu-OtBu) or Lys(Boc-Glu-OtBu) and wherein at least the side chains of Glu, Asp, and Lys bear protecting groups; and
  (i-b) cleaving the precursor peptide off the resin by means of an cleavage composition comprising trifluoroacetic acid (TFA), wherein said solution S obtained from step (i) comprises trifluoroacetic acid (TFA), water and one or more scavengers selected from thiol scavengers and/or silane scavengers;
(ii) precipitation of the peptide of step (i) by means of mixing solution S with an anti-solvent consisting of diisopropyl ether and acetonitrile, wherein the volume ratio (diisopropyl ether:acetonitrile) is in the range of from (3:1) to (5:1); and
(iii) isolating the precipitate obtained from step (ii), preferably by means of filtration and/or centrifugation.

The person skilled in the art will immediately notice that the peptide of formula I refers to a derivative of the plain Liraglutide polypeptide strand, written in one-letter code:

HAEGTFTSDVSSYLEGQAAKEFIAWLVRGRG,    (SEQ ID NO: 4)

wherein the lysyl moiety in position 20 of the amino acid sequence (Lys20, K20) is modified. More in detail, the epsilon amino group of the Lys20 is conjugated to the gamma carboxyl residue of a glutamyl moiety (γ-Glu, γ-E) via an amide bond. This glutamyl moiety will typically bear a free alpha carboxyl group. The glutamyl moiety may either be conjugated to a palmitic acid=hexadecanoic acid moiety via its amino group, or may bear a free —NH2 (alpha amino group, Nα).

Preferably, the peptide of formula I is (essentially) free of any protecting groups and has no other modifications at amino acid side chains except the moiety of Lys20. Accordingly, the peptide of formula I is preferably the fully unprotected peptide, which is preferably not further modified.

The term "protecting group" as used herein may be understood in the broadest sense as a group which is introduced into a molecule by chemical modification of a functional group to block said group from reaction in subsequent process steps, e.g. to prevent side reactions of the amino acid side chains. Examples of amino protecting groups are the Boc and Fmoc groups, examples of carboxylic acid protecting groups are unreactive esters such as methyl esters, benzyl esters, or tert. butyl esters.

As used herein, the terms "resin" and "[resin]" may be understood in the broadest sense as a support structure usable for SPPS. Preferably, the resin has a bead-like structure. The terms "resin", "solid phase" and "support" are used exchangeably herein.

In the context of the present application, the term "scavengers" is used to refer to compounds which are added to the reaction mixture in order to suppress side reactions during cleavage of a peptide from the resin after SPPS and/or during removal of protecting groups. Typical scavengers used in a cleavage composition are water, "thiol scavengers" (e.g. EDT, DTE, DTT, and beta-mercaptoethanol) and "silane scavengers" (e.g. TES and TIPS).

Further commonly used scavengers comprise ethyl methyl sulfide, thioanisole, anisole, m- or p-cresol, 2-Me-indole, Ac-Trp-OMe, or tryptamine. The person skilled in the art is well aware of a large variety of scavengers usable.

In a preferred embodiment of the invention, step a) of the purification method involves obtaining a dried crude Liraglutide precipitate and dissolving said dried precipitate in a suitable buffer at a pH selected from the range of 7.0 to 7.8, preferably 7.0 to 7.5, in order to obtain a liquid composition C comprising Liraglutide and at least one unwanted component. In a preferred embodiment, step a) comprises dissolving a dried crude Liraglutide peptide in an aqueous phosphate buffer AB0 at a pH selected from the range of 6.6-7.9, preferably 7.0 to 7.8, and most preferably 7.0 to 7.5. Particularly preferred phosphate buffers are sodium hydrogen phosphate or ammonium hydrogen phosphate at a pH selected from the range of 7.0 to 7.5.

In a preferred embodiment of the invention, the crude Liraglutide peptide is obtained by solid phase peptide synthesis, followed by trifluoroacetic acid mediated cleavage and peptide precipitation from the cleavage composition.

For the purpose of the present application, the terms "raw" and "crude" are used interchangeably to designate preparations of a peptide such as Liraglutide, which are essentially a direct product of synthesis and isolation processes and have not yet been submitted to specific purification steps. Chemical synthesis usually yields crude Liraglutide preparations having a purity of around 50 to 70%. It should however be understood that the liquid composition C may be characterized by any degree of purity below 100% (e.g. a purity above 30, 40, 50, 60, 70, 80, or 90%) and that the present invention may also be advantageously applied to partially purified Liraglutide compositions.

In the context of the present invention, the term "purified" is used to designate peptide compositions which have been subjected to specific purification steps, e.g. to preparative chromatography. Such compositions may be highly or partially purified.

Unless noted otherwise, peptide purity is indicated herein as "HPLC purity", i.e. as relative peak area observed in analytical reversed phase high performance liquid chromatography (RP-HPLC) with UV detection at a wavelength between 205 and 230 nm, i.e. at the absorption maximum of the peptide bond. In other words, the value is determined as % area of a given peak area divided by the sum of the areas of all observed peaks in a chromatogram obtained by analytical RP-HPLC with UV detection at a wavelength between 205 and 230 nm. This measure is common practice in the field, and the skilled person will routinely devise a product specific RP-HPLC protocol and perform the quantification according to the established guidelines set out in the United States Pharmacopeia. The suitability of the RP-HPLC protocol for the detection of peptidic contaminations is routinely assessed by determining the peak purity by LC-MS. Under the assumption that, due to their similar structure, all peptidic components have the same absorption, the RP-HPLC purity can be used as a proxy for a purity expressed as mass percentage [% (w/w)].

The skilled person is well aware of how to prepare samples for chromatographic purification. For example, a dried crude Liraglutide preparation may be dissolved by gentle stirring in an aqueous phase while adjusting temperature and pH as appropriate. The present inventors found aqueous buffers of a pH of 6.6-7.9, preferably 7.0-7.8, and in particular a pH of 7.0-7.5, particularly suitable for dissolving crude Liraglutide preparations. As further examples, the sample may be kept under inert gas or subjected to ultrasound treatment, may be subjected to decarboxylation reactions, may be subjected to specific hydrolysis, and/or may be separated from non-liquid components by filtration or centrifugation. The sample concentration may be adjusted, inter alia, by drying, freeze-drying, partial evaporation of solvent, or ultrafiltration, and/or by dissolving or diluting the peptide preparation in a sample loading buffer, as the case may be.

Reversed phase high performance liquid chromatography (RP-HPLC) is well-known and widely used for peptide purification and analysis of peptide samples, i.e. for preparative as well as analytical purposes. The technique is based on hydrophobic association between the various components of a sample and a hydrophobic stationary phase, which association is disrupted by a solvent comprised in the mobile phase. Differential elution of the sample's components is generally achieved by gradually increasing the concentration of the solvent within the mobile phase.

From a practical perspective, this gradient is usually obtained by varying the proportions of a first and second elution buffer making up the mobile phase: The first buffer, dubbed Buffer A by convention, comprises low amounts of the solvent in a suitable aqueous buffer, while the second buffer, dubbed Buffer B by convention, comprises high amounts of the solvent in said aqueous buffer. Hence, by increasing the proportion of Buffer B in the mobile phase, more hydrophobic components can be eluted from the stationary phase.

As used herein, the term HPLC also includes ultra high performance liquid chromatography (UHPLC, also designated as UPLC). In one preferred embodiment, HPLC is UHPLC. More preferably, UHPLC is reversed phase UHPLC and may thus also be designated as RP-UHPLC. Therefore, in a particularly preferred embodiment, HPLC is RP-UHPLC.

In the context of the present application, the expression "hydrocarbon bonded silica" refers to stationary chromatographic phases made from porous silica particles or silica gels having chemically bonded hydrocarbon moieties at their surface. It is understood that the type of chemical bond as well as the chemical nature of the bonded hydrocarbon moieties may vary. For example, a stationary phase for use with the present application may be made from porous silica particles having chemically bonded hydrocarbon moieties of 4 to 18, preferably 8 to 18, carbon atoms. Such hydrocarbon moieties are preferably linear alkyl chains. Preferred types of hydrocarbon bonded silica have hydrocarbon moieties with four (C4), six (C6), eight (C8), ten (C10), twelve (C12), fourteen (C14), sixteen (C16), or eighteen (C18) carbon atoms. Particularly preferred types of hydrocarbon bonded silica have unbranched alkyl chains of four (C4), eight (C8), twelve (C12) or eighteen (C18) carbon atoms, i.e. butyl, octyl, dodecyl, or octadecyl moieties. C8 bonded silica, in particular n-octyl bonded silica, and/or C18 bonded silica, in particular n-octadecyl bonded silica, are even more preferred stationary phases for use in steps b), c), and optionally d) of a method according to the present invention. The stationary phase used in steps b) and c) and optionally d) may be the same or different in each of the steps. Preferably the stationary phase is the same. Particularly preferably, a single stationary phase (i.e., a single column) is used in steps b) and c) and optionally d).

In the context of the present application, the expression "08 bonded silica" is used to designate stationary chromatographic phases made from porous silica particles or silica gels having at their surface chemically bonded C8 hydrocarbon moieties, preferably linear octyl, i.e. n-octyl, moieties. Further, the expression "012 bonded silica" is used to designate stationary chromatographic phases made from porous silica particles or silica gels having at their surface chemically bonded C12 hydrocarbon moieties, preferably linear dodecyl, i.e. n-dodecyl, moieties. Likewise, the terms "C18 bonded silica" or "ODS" are used herein interchangeably to refer to stationary chromatographic phases made from porous silica particles or silica gels having at their surface chemically bonded C18 hydrocarbon moieties, preferably linear octadecyl, i.e. n-octadecyl, moieties.

A wide range of hydrocarbon bonded silica materials is commercially available. Examples of stationary phases which can be used in present invention are Daisogel™ C18 ODS, Daiso ODS-Bio, Daiso-ODS-A-HG C18, Daisogel™ C8-Bio, YMC ODS-A, YMC Triart C8-L, Luna C8, Luna C18, Kromasil™ C18, and Kromasil™ C8 produced by Daiso, YMC, Phenomenex, and AkzoNobel, respectively.

The silica particles may be of 2 to 200 micrometer, preferably 2.5 to 20 micrometer, preferably 5-15 micrometer, and most preferably 10 micrometer, in diameter and may have a pore size of 50 to 1000 Å, preferably of 80 to 400 Å, preferably of 100 to 300 Å, most preferably of (about) 100 Å.

The mobile phases used in the RP-HPLC steps of the present invention generally comprise an aqueous component and acetonitrile as a solvent. Additional components such as organic modifiers may be present. Elution is effected by gradually increasing the concentration of the acetonitrile as a solvent. Without wishing to be bound by any theory, it is believed that the solvent competes with the association of the components of composition C to the stationary phase. In order to maintain a linear velocity, the skilled practitioner will adjust the flow rate of the mobile phase depending on the column diameter and taking account of the specifications of the equipment and stationary phase employed.

Step b) of the method according to the present invention, i.e. the first dimension of the RP-HPLC purification scheme, is carried out at a pH value between 7.0 and 7.8, e.g. at a pH value of 7.0, 7.1, 7.2, 7.3, 7.4, 7.5, 7.6, 7.7, or 7.8, preferably at a pH value between 7.5 and 7.8. The pH value is adjusted at the temperature at which the step will be carried out by use of a phosphate buffer in the aqueous component of the mobile phase. Preferably, the phosphate buffer is used at a concentration of 5 to 50 mM. Any type of phosphate buffer may be used, e.g. sodium phosphate, potassium phosphate, or ammonium phosphate. In one preferred embodiment, the aqueous phosphate AB1 buffer in step b) is ammonium phosphate buffer, preferably at a concentration of 5 to 50 mM. It is understood that any type of acetonitrile gradient may be used for the elution of Liraglutide from the stationary phase and that the gradient profile impacts the purification achievable in this step. In a preferred embodiment, the gradient in step b) is from 19 to 67% (v/v) acetonitrile. Particularly preferred is a linear gradient from 19 to 67% (v/v) acetonitrile.

Step c) of the method according to the present invention, i.e. the second dimension of the RP-HPLC purification scheme, is carried out at a pH value below 3. The pH value is determined by the presence of 0.05-0.5% (v/v) TFA in the aqueous component of the mobile phase. In a preferred embodiment, the TFA concentration within the mobile phase used in step c) is selected from the range of 0.05-0.2% (v/v), preferably 0.05-0.1% (v/v). It is understood that any type of acetonitrile gradient may be used for the elution of Liraglutide from the stationary phase and that the gradient profile impacts the purification achievable in this step. In a preferred embodiment, the gradient in step c) is from 31 to 100% (v/v) acetonitrile. Particularly preferred is a linear gradient from 31 to 100% (v/v) acetonitrile.

Optionally, step d), i.e. a third RP-HPLC purification dimension, may be carried out in order to further improve the purity of the Liraglutide preparation. Said step is carried out at a pH value between 7.0 and 7.8, e.g. at a pH value of 7.0, 7.1, 7.2, 7.3, 7.4, 7.5, 7.6, 7.7, or 7.8, preferably at a pH value between 7.5 and 7.8. The pH value is adjusted at the temperature at which the step will be carried out by use of a buffer AB2 in the aqueous component of the mobile phase. Preferably, the buffer is used at a concentration of 5 to 100 mM. Any type of buffer may be used, e.g. sodium phosphate, potassium phosphate, ammonium phosphate, sodium acetate, potassium acetate, sodium carbonate, or potassium carbonate.

In a preferred embodiment of the invention, said aqueous buffer AB2 is selected from the group consisting of a mixture of sodium dihydrogen phosphate and disodium hydrogen phosphate, a mixture of potassium dihydrogen phosphate and dipotassium hydrogen phosphate, potassium acetate, and sodium acetate.

In a particularly preferred embodiment, sodium acetate buffer is used. It is understood that any type of acetonitrile gradient may be used for the elution of Liraglutide from the stationary phase and that the gradient profile impacts the purification achievable in this step. In a preferred embodiment the gradient in step c) is from 19 to 67% (v/v) acetonitrile. Particularly preferred is a linear gradient from 19 to 67% (v/v) acetonitrile.

In one embodiment of the present invention, the purification method further comprises a step e) of size exclusion chromatography.

This step e) may be optionally carried out after any step a)-d). Preferably, it is carried out after step c) or, if present, after step d).

Size exclusion liquid chromatography is well known for analytical as well as preparative purposes in peptide chemistry. The method relies on the use of porous materials a stationary phase, where the pore size is selected such that only some components of a sample can enter into some of the pores. As a result, the accessible volume encountered by the various components varies, depending on each component's apparent molecular size. Hence, the components of the sample will elute from the column in the order of their apparent size, with large molecules eluting first. Ideally, the components of the sample do not interact with the surface of the stationary phase, such that differences in elution time result exclusively from differences in the solute volume each component can enter. Consequently, the composition of the mobile phase does not directly affect chromatographic resolution and can be adjusted with a view to sample properties or the needs of downstream processing steps.

It is envisaged to employ size exclusion chromatography after the RP-HPLC steps either for the separation of high molecular weight contaminants or for the removal of salt. Depending on the purpose, the skilled person will select a stationary phase with a suitable particle and pore size distribution. Preferred stationary phases for use with the present invention have pore sizes of 100-300 Å (e.g. 100, 125, 145, 200 or 300 Å) or molecular weight ranges of 0.7-10 kDa (e.g. <0.7, <1.5, 0.1-7, 1-5 or <10 kDa) or 1.5-30 kDa and particle sizes of 2-5 micrometer or 20-300 micrometer. Suitable commercial products comprise, e.g., Sephadex® G50 (GE Healthcare Life Sciences), WatersAcquity™ BEH 200, Phenomenex Yarra™ SEC-2000, Tosoh Biosciences TSKgel® SuperSW2000, Sephadex® G-25 (GE Healthcare Life Sciences), Toyopearl® HW-40 (Tosoh Biosciences), Superdex® peptide (GE Healthcare Life Sciences) and Superdex®30 (GE Healthcare Life Sciences). Preferred mobile phases include ultra pure water, 10 mM aqueous sodium hydrogen phosphate at pH 7.5, or any buffer/solvent system compatible with the sample.

In a preferred embodiment, the method further comprises step f) of desalting the peptide, preferably wherein desalting is performed by ion exchange chromatography, by size exclusion chromatography, or by ultrafiltration.

This step f) may be optionally carried out after any step a)-e). Preferably, it is carried out after step c) or, if present, after step d) or e). In one embodiment of the invention, steps e) and f) may optionally be the same, i.e. desalting may be performed by means of size exclusion chromatography using a suitable stationary phase. For instance, the step of desalting may comprise using GE Healthcare Life Sciences Sephadex® G-25, Sephadex® G-50, or Superdex® peptide as a stationary phase and ultra pure water, optionally mixed with an organic solvent such as an alcohol or acetonitrile, as a mobile phase for isocratic elution.

As used herein, the expressions "desalting" and "removal of salt" are used interchangeably for any method step which reduces a sample's salt content. For example, the salt content may be decreased by more than 50%, more than 60%, more than 70%, more than 80%, more than 90%, more than 95%, or more than 99%. In a preferred embodiment, the amount of buffer anions is reduced to levels below the detection level. Desalting may be performed by any suitable method. Besides size exclusion chromatography as described above, commonly used and well known options are dialysis, ion exchange chromatography and ultrafiltration. Ultrafiltration is a pressure-driven separation process, which relies on the use of a semipermeable membrane allowing for small buffer and solvent molecules to pass, but retaining the peptide of interest.

For the purpose of the present invention, it is preferred to use membranes having a molecular weight cut-off of not more than 3 kDa, e.g. 3 kDa, 2 kDa, 1 kDa, or below. The liquid passing through the membrane is referred to as "permeate" or "filtrate", while the sample retained by the membrane is referred to as "retentate". To avoid clogging of membrane pores, a tangential flow filtration format (aka. cross flow filtration) is advantageously employed. For the purpose of the present invention, it is preferred to use membranes compatible with organic solvents such as acetonitrile. In a particularly preferred embodiment, a polyethersulfone membrane with a molecular weight cut off of 1 kDa is used. It should however be understood that, as long as it provides a suitable molecular weight cut-off, the filter may be of any material known in the context of filtration, such as, e.g., plastic (e.g., nylon, polystyrene), metal, alloy, glass, ceramics, cellophane, cellulose, or composite material. The filter may be hydrophobic or hydrophilic. The surface of the filter may be neutral or positively charged or negatively charged.

The skilled person will routinely combine the methods of the present invention with suitable read-out techniques. For example, chromatographic steps may be monitored by following the UV absorbance of the eluate at a wavelength of 205-230 nm or 280 nm, and/or by following the eluate's conductivity. Moreover, chromatography may be combined with online or offline analysis by mass spectrometry, size exclusion UHPLC, ion exchange UHLPC, and/or reversed phase UHPLC, enzyme-linked immunosorbent assays (ELISA), and/or cell-based functional assays.

In order to avoid deterioration of the peptide quality, the skilled person will carefully and routinely optimize the conditions of the purification steps including the sample storage. To this end, fractions may be, inter alia, pooled, precipitated, spray-died, freeze-dried, frozen, refrigerated, diluted, concentrated, and/or mixed with stabilizing buffers, bases, acids, or other substances. It is good practice to handle sensitive materials under stabilizing conditions. For example, it may be advantageous to work at reduced temperature, e.g. in the range of 4° C. to 15° C. in order to compensate for otherwise destabilizing conditions. As a further example, it may be advantageous to freeze-dry Liraglutide preparations, preferably at a pH selected from a range of 6.6-7.9, preferably 7.0 to 7.8, and most preferably 7.0 to 7.5.

In a preferred embodiment of the invention, all or parts of the chromatographic purification steps b) and/or c) and/or step d), if present, is/are carried out at a temperature selected from the range of 4-25° C., preferably 4-20° C., and most preferably 4-10° C. Likewise, all or parts of any of the optional further purification steps, i.e. size exclusion chromatography step (step e)) and/or an desalting step (step f)) may be carried out at a temperature selected from the range of 4-25° C., preferably 4-20° C., and most preferably 4-10° C.

In a particularly preferred embodiment, the method of the present invention comprises:
a) Providing a liquid composition C comprising Liraglutide and at least one unwanted component, optionally dissolved in an aqueous phosphate buffer of a pH selected from the range of 7.0 to 7.5;
b) Subjecting the composition C to a first reversed phase HPLC purification at a pH between 7.0 and 7.8, wherein a hydrocarbon bonded silica is used as a stationary phase, a mixture comprising acetonitrile and an aqueous ammonium phosphate buffer at a concentration of 5 to 50 mM is used as a mobile phase, and elution is effected by gradually increasing the acetonitrile concentration within the mobile phase from 19 to 67% (v/v) acetonitrile while collecting Liraglutide containing fractions; and
c) Subjecting the pooled Liraglutide containing fractions obtained in step b) to a second reversed phase HPLC purification at a pH below 3.0, wherein a hydrocarbon bonded silica is used as a stationary phase, a mixture comprising 0.05-0.5% (v/v) trifluoroacetic acid solution and acetonitrile is used as a mobile phase, and elution is effected by gradually increasing the acetonitrile concentration within the mobile phase from 31 to 100% (v/v) acetonitrile while collecting fractions containing purified Liraglutide;
d) Optionally, subjecting the Liraglutide obtained in step c) to a third reversed phase HPLC purification at a pH between 7.0 and 7.8, wherein a hydrocarbon bonded silica is used as a stationary phase, a mixture of an aqueous buffer AB2 with acetonitrile is used as a mobile phase, and elution is effected by gradually increasing the acetonitrile concentration within the mobile phase from 19 to 67% (v/v) acetonitrile while collecting fractions containing purified Liraglutide;

e) Optionally, subjecting the Liraglutide obtained in any of steps c) or d) to size exclusion chromatography; and f) Optionally, subjecting the Liraglutide obtained in any of steps c), d) or e) to desalting the peptide, preferably wherein desalting is performed by ion exchange chromatography, by size exclusion chromatography, or by ultrafiltration;

wherein the step b) and step c) and, if present steps d), e) and/or f) are carried out at a temperature selected from the range of 4-25° C.;

wherein preferably the stationary phase used in steps b) and c) and step d), if present, is C8 bonded silica or C18 bonded silica.

As is shown in the examples below, the methods of the present invention enable the preparation of very pure Liraglutide, and purities above 99.0% can be routinely achieved. Nevertheless, traces of several deletion products could be detected. These are in particular traces of peptides consisting of 27-30 continuous amino acids, which differ from Liraglutide's molecular structure in that they are lacking up to four amino acids out of the primary sequence of the Liraglutide peptide backbone (SEQ ID NO:4), and which may optionally have additional alterations at 2-5 amino acid side chains or at the (N-ε-(γ-Glu(N-α-hexadecanoyl)))-substituent at the Lys moiety corresponding to Lys 20 of SEQ ID No:4. In other words, Liraglutide deletion variants may be defined as peptides of 27 to 30 amino acid moieties in length, which share at least 80% homology to SEQ ID NO:4, calculated over the entire length of SEQ ID NO:4, and which optionally comprise a modification at the lysine moiety homolog to $Lys^{20}$ of SEQ ID NO:4.

The person skilled in the art will immediately understand that such Liraglutide deletion variants may optionally, but not necessarily, be truncated at the N- and/or C-terminal amino acid moieties. Additionally or alternatively, also non-terminal amino acid moieties may be missing. As mentioned above, sequence homology may be understood as sequence homology determined by BLAST (Basic Local Alignment Search Tool) of the National Center for Biotechnology Information (NCBI) in the version of the filing date of the present application. That means that each amino acid moiety is aligned to its counterpart in the sequence to be compared, sparing missing amino acid moieties in between and percentage homology is calculated over the entire length of SEQ ID NO:4.

In the experiments conducted, no peptidic contaminant was detected at a relative abundance above 0.3% (w/w), determined as relative peak area measured by RP-UHPLC at 220 nm (cf., exemplifying FIG. 2). This also reflects an aspect and preferred embodiments of the present invention. The relative peak area was determined as % area of a given peak area divided by the sum of the areas of all observed peaks in a chromatogram obtained by analytical RP-HPLC with UV detection at 220 nm. This can be done using any product-specific RP-HPLC protocol suitable for the detection of peptidic contaminants. The suitability of the analytic method is routinely assessed in terms of principal peak purity determined by LC-MS. The person skilled in the art will immediately understand that, due to their similar structure, all peptidic components have the same or at least comparable response factors, such that the relative peak area measured by RP-HPLC at 220 nm correlates well to the relative abundance of a given peptide expressed in weight percent relative to the summed mass of all peptide components, indicated in % (w/w).

Therefore, a further aspect of the present invention relates to a composition LC comprising Liraglutide obtainable from a method according to any embodiment of the present invention, characterized in that said composition contains Liraglutide at a purity above 98.8%, preferably above 99%, determined as the relative peak area observed in analytical RP-HPLC with UV detection at 220 nm, and does not contain more than 0.5%, determined as the relative peak area observed in analytical RP-HPLC with UV detection at 220 nm, of any single Liraglutide derivative, Liraglutide truncation variant, derivative of a Liraglutide truncation variant, Liraglutide deletion variant, or derivative of a Liraglutide deletion variant.

A further aspect of the present invention relates to a composition LC comprising Liraglutide obtainable from a method according to any embodiment of the present invention, characterized in that said composition contains Liraglutide at a purity above 98.8%, preferably above 99%, determined as the relative peak area observed in analytical RP-HPLC with UV detection at 220 nm, and does not contain more than 0.3% of any single Liraglutide deletion variant, determined as the relative peak area observed in analytical RP-HPLC with UV detection at 220 nm, wherein a Liraglutide deletion variant is a peptide of 27 to 30 amino acids in length, which shares at least 80% homology to SEQ ID NO:4, over the entire length of SEQ ID NO:4, and which optionally comprises a modification at the lysine moiety homolog to $Lys^{20}$ of SEQ ID NO:4.

Therefore, a further aspect of the present invention relates to a composition LC comprising Liraglutide obtainable from a method according to any embodiment of the present invention, characterized in that said composition contains Liraglutide at a purity above 98.8%, preferably above 99%, determined as the relative peak area observed in analytical RP-HPLC with UV detection at 220 nm, and does contain detectable levels, but not more than 0.3% of any single Liraglutide deletion variant, determined as the relative peak area observed in analytical RP-HPLC with UV detection at 220 nm, wherein a Liraglutide deletion variant is a peptide of 27 to 30 amino acids in length, which shares at least 80% homology to SEQ ID NO:4, over the entire length of SEQ ID NO:4, and which optionally comprises a modification at the lysine moiety homolog to $Lys^{20}$ of SEQ ID NO:4.

A further aspect of the present invention refers to a composition LC comprising Liraglutide obtainable from a method according to any embodiment of the present invention, characterized in that said composition contains Liraglutide at a purity above 98.8% (w/w), referred to the summed mass of all peptide components, and does not contain one or more polypeptides of an amino acid sequence length of 27 to 30 consecutive amino acids having at least 80% homology to SEQ ID NO:4, over the entire sequence of SEQ ID NO:4, optionally comprising a modification at the lysine moiety homolog to $Lys^{20}$ of SEQ ID NO:4, at a concentration above 0.3% (w/w), referred to the summed mass of all peptide components.

The composition LC may preferably comprise traces (e.g., 0.001 ppm (w/w) or more, 0.01 ppm (w/w) or more, or 0.1 ppm (w/w) or more, or 1 ppm (w/w) or more) of such polypeptides of an amino acid sequence length of 27 to 30 consecutive amino acids having at least 80% homology to SEQ ID NO:4, over the entire length of SEQ ID NO:4, optionally comprising a modification at the lysine moiety homolog to Lys$^{20}$ of SEQ ID NO:4.

Highly preferably, the composition LC comprises between 0.001 ppm and 0.3% (w/w), even more preferably between 0.01 ppm and 0.2% (w/w), even more preferably between 0.1 ppm and 0.1% (w/w), even more preferably between 1 ppm and 0.05% (w/w), in particular between 1 ppm and 0.01% (w/w), of such polypeptides of an amino acid sequence length of 27 to 30 consecutive amino acids having at least 80% sequence homology, in particular at least 90% sequence homology, to SEQ ID NO:4, over the entire length of SEQ ID NO:4, optionally comprising a modification at the lysine moieties homolog to Lys$^{20}$ of SEQ ID NO:4.

Preferably, the composition LC contains Liraglutide at a purity above 99.1% (w/w), above 99.2% (w/w), above 99.3% (w/w), above 99.4% (w/w), above 99.5% (w/w), above 99.6% (w/w), above 99.7% (w/w), above 99.8% (w/w) or above 99.9% (w/w), referred to the summed mass of all peptide components.

In a preferred embodiment, the composition LC does not contain one or more polypeptides of an amino acid sequence length of 27 to 30 consecutive amino acids having at least 80%, more preferably at least 90%, in particular at least 95% sequence homology to SEQ ID NO:4, over the entire length of SEQ ID NO:4, optionally comprising a modification at the lysine moieties homolog to Lys$^{20}$ of SEQ ID NO:4.

In a more preferred embodiment, the composition LC does not contain polypeptides of an amino acid sequence length of 27 to 30 consecutive amino acids having the respective amino acid sequence or sequence fractions corresponding to SEQ ID NO:4, over the entire length of SEQ ID NO:4, and, optionally comprising a modification at the lysine moieties homolog to Lys20 of SEQ ID NO:4.

According to a preferred embodiment, the composition LC does not contain the above mentioned Liraglutide deletion variants at a total concentration above 0.25% (w/w), 0.20% (w/w), 0.15% (w/w), 0.1% (w/w), 0.05% (w/w), or 0.01% (w/w), referred to the summed mass of all peptide components.

More preferably, the composition LC does not contain a specific impurity of a Liraglutide deletion variant at an individual concentration above 0.1% (w/w), 0.05% (w/w), or 0.01% (w/w), referred to the summed mass of all peptide components.

Particularly preferably, the composition LC contains one or more Liraglutide deletion variants at a total concentration between 0.001 ppm and 0.3% (w/w), more preferably 0.01 ppm and 0.1% (w/w), in particular between 0.01 ppm and 0.01% (w/w), referred to the summed mass of all peptide components.

A further aspect of the present invention relates to a composition LC comprising Liraglutide obtainable from a method according to any embodiment of the present invention, characterized in that said composition contains Liraglutide at a purity above 98.8%, preferably above 99%, and does not contain more than 0.5%, preferably 0.3%, more preferably 0.2%, and most preferably 0.1% of each of i) any Liraglutide derivative, where the indole moiety in the side chain of Trp at position 25 is oxidized by incorporation of a single oxygen atom, and/or ii) any Liraglutide derivative, where the indole moiety in the side chain of Trp at position 25 is oxidized by incorporation of two oxygen atoms and/or of iii) any Liraglutide derivative comprising kynurenine instead of Trp at position 25 and/or of iv) a Liraglutide deletion variant lacking Gly$^{31}$.

A further aspect of the present invention relates to a composition LC comprising Liraglutide obtainable from a method according to any embodiment of the present invention, characterized in that said composition contains Liraglutide at a purity above 98.8%, preferably above 99%, and does contain detectable levels, but not more than 0.5%, preferably not more than 0.3%, more preferably not more than 0.2%, and most preferably not more than 0.1% of each of i) any Liraglutide derivative, where the indole moiety in the side chain of Trp at position 25 is oxidized by incorporation of a single oxygen atom, and/or of ii) any Liraglutide derivative, where the indole moiety in the side chain of Trp at position 25 is oxidized by incorporation of two oxygen atoms and/or of iii) a Liraglutide derivative comprising kynurenine instead of Trp at position 25 and/or of iv) a Liraglutide deletion variant lacking Gly$^{31}$.

A further aspect of the present invention relates to a composition LC comprising Liraglutide obtainable from a method according to any embodiment of the present invention, characterized in that said composition contains Liraglutide at a purity above 98.8%, preferably above 99%, and does not contain more than 0.5%, preferably 0.3%, more preferably 0.2%, and most preferably 0.1% of each of i) any Liraglutide derivative, where the indole moiety in the side chain of Trp at position 25 is oxidized by incorporation of a single oxygen atom, and of ii) any Liraglutide derivative, where the indole moiety in the side chain of Trp at position 25 is oxidized by incorporation of two oxygen atoms and of iii) a Liraglutide derivative comprising kynurenine instead of Trp at position 25 and of iv) a Liraglutide deletion variant lacking Gly$^{31}$.

A further aspect of the present invention relates to a composition LC comprising Liraglutide obtainable from a method according to any embodiment of the present invention, characterized in that said composition contains Liraglutide at a purity above 98.8%, preferably above 99%, and does contain detectable levels, but not more than 0.5%, preferably not more than 0.3%, more preferably not more than 0.2%, and most preferably not more than 0.1% of each of i) any Liraglutide derivative, where the indole moiety in the side chain of Trp at position 25 is oxidized by incorporation of a single oxygen atom, and of ii) any Liraglutide derivative, where the indole moiety in the side chain of Trp at position 25 is oxidized by incorporation of two oxygen atoms and of iii) a Liraglutide derivative comprising kynurenine instead of Trp at position 25.

Preferably, the above percentages are determined as the relative peak area observed in analytical RP-HPLC with UV detection at 220 nm, Alternatively, the above percentages may be referred to the summed mass of all peptide components.

According to a preferred embodiment, the composition LC comprises Liraglutide obtainable from a method according to any embodiment of the present invention, characterized in that said composition contains Liraglutide at a purity above 98.8%, preferably above 99%, determined as the relative peak area observed in analytical RP-HPLC with UV detection at 220 nm, and does contain detectable levels, but not more than 0.5%, preferably not more than 0.3%, more preferably not more than 0.2%, and most preferably not more than 0.1%, determined as the relative peak area observed in analytical RP-HPLC with UV detection at 220 nm, of each of i) any Liraglutide derivative, where the indole moiety in the side chain of Trp at position 25 is oxidized by incorporation of a single oxygen atom, and/or of ii) any Liraglutide derivative, where the indole moiety in the side chain of Trp at position 25 is oxidized by incorporation of two oxygen atoms and/or of iii) a Liraglutide derivative comprising kynurenine instead of Trp at position 25 and/or of iv) a Liraglutide deletion variant lacking Gly$^{31}$.

A further aspect of the present invention relates to a composition LC comprising Liraglutide obtainable according to any embodiment of the present invention, characterized in that said composition contains Liraglutide at a purity above 99%, preferably above 99.5%, determined as a) the relative peak area observed in analytical RP-HPLC with UV detection at 220 nm, and b) as the relative peak area observed in analytical size exclusion chromatography with UV detection at 220 nm.

Preferably, in the composition LC, the Liraglutide is obtained from a method according to the present invention.

The following Figures and Examples, including the experiments conducted and the results achieved, are provided for illustrative purposes only and are not to be construed as limiting the scope of the claims.

BRIEF DESCRIPTION OF THE FIGURES

FIG. 1 shows the sequence alignment of selected glucagon-like peptides. Moieties sharing identity with the GLP-1 sequence are written in bold.

EXAMPLES

Example 1: Determination of Purification Conditions

Figure 2:
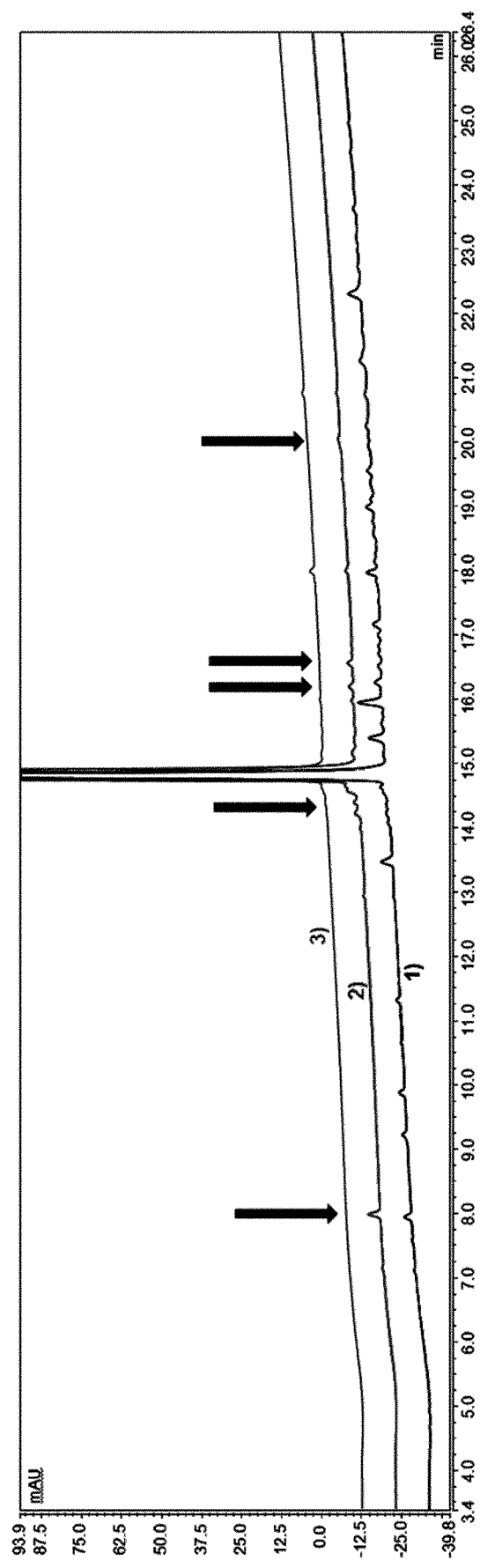
FIG. 2: Two dimensional Liraglutide purification of Example 2. Overlays of the analytical RP-UHPLC traces of the crude Liraglutide preparation used as starting material (crude, indicated as 1)) and of the pooled fractions obtained after the first purification dimension (1D, pool (NH$_4$)$_3$PO$_4$, pH 7.5, indicated as 2)) and second purification dimension (2D, pool TFA, indicated as 3)) are shown. Arrows highlight unwanted components, which were not removed in the first dimension, but in the second dimension.

Small scale experiments were carried out to identify suitable purification conditions. The seven mobile phase buffers given in column 2 of Table 2 were tested each on four different stationary phases as indicated in line 1, columns 3-6 of Table 2. Each mobile phase buffer was used to prepare a Buffer A consisting of 3% (v/v) acetonitrile in an aqueous solution of said buffer, and a Buffer B consisting of 67 or 80% (v/v) acetonitrile in an aqueous solution of said buffer. The buffer concentrations in the aqueous solutions were between 20 and 400 mM, depending on the nature of the mobile phase buffer.

Each line of Table 2 represents four different one dimensional RP-HPLC runs, namely one run for each of the four stationary phases tested. For each of said runs, the Buffers A and B prepared with the mobile phase buffer indicated in column 2 the respective line were used. The following general protocol applied: Crude Liraglutide peptide produced by Fmoc SPPS (purity >=60%) was dissolved in Buffer A, and 18 mg each applied in parallel experiments to the four different stationary phases consisting of C8 or C18 bonded silica (column dimensions: 250×4.6 mm). The protocol generally involved equilibration of the column for 15 min in Buffer A, sample loading, and elution for 1 min with Buffer A alone, followed by a gradient of 20-100% Buffer B. The flow rate was of 0.63 ml/min. Fractions of 0.37 ml were collected and analyzed by reversed phase UHPLC. Table 2 below indicates the purities determined in the purest fraction of each experiment in terms of relative peak area. Said relative peak area was calculated by dividing the Liraglutide peak area by the sum of all peak areas observed in analytical UHPLC, i.e. the area of the Liraglutide peak was expressed in percent of the total peak area.

TABLE 2

| | Buffer | YMC Triart C8-L | Luna PREP C8 | Kromasil C18 | Daiso ODS-Bio |
|---|---|---|---|---|---|
| 1 | NH$_4$HCO$_3$ | 95.40% | 96.56% | 96.86% | 97.18% |
| 2 | (NH$_4$)$_3$PO$_4$ | 97.84% | 98.02% | 98.10% | 97.76% |
| 3 | NH$_4$OAc | 95.84% | 96.71% | 94.79% | 93.97% |
| 4 | TEAP | 94.76% | 95.58% | 95.66% | 95.52% |
| 5 | AcOH | 94.18% | 91.79% | 94.90% | 95.74% |
| 6 | H$_3$PO$_4$ | 95.55% | 95.01% | 95.37% | 95.33% |
| 7 | TFA | 96.97% | 96.24% | 97.00% | 96.93% |

Conclusions:
1. Various C8 and C18 stationary phases give similar results. For each of the stationary phases, the following observations applied:
2. Under neutral to slightly basic (7.0≤pH<8.0) conditions, ammonium phosphate buffer is surprisingly superior to other buffers tested (cf. columns 3-6 of lines 1-4).
3. Under acidic conditions (pH<3.0), TFA buffer is surprisingly superior to other buffers tested (cf. columns 3-6 of lines 5-7).

Example 2: Two Dimensional RP-HPLC Purification

The purification involved a chromatographic purification at pH 7.5 in the first dimension, followed by a chromatographic purification under acidic conditions in the second dimension.

A 5 cm MODcol column (Grace) packed with C8-bonded silica (approx. bed-depth 32 cm) was used on a preparative HPLC system (Knauer HPLC pump 1800) with detection at 220 nm (Knauer smartline UV detector 2500) and an automated fraction collector (Büchi C-660). The same stationary phase was used in both dimensions of the purification protocol. Crude Liraglutide produced by Fmoc SPPS (purity >60%) was used as a starting material. The sample was loaded on the column at a flow rate of 90 ml/min. The detailed elution protocols for each step are given in Tables 3 and 4 below. The buffer concentration in the aqueous part of the mobile phase used in the first dimension was 20 mM.

TABLE 3

| Parameters first purification dimension | |
|---|---|
| Sample loading buffer | aqueous ammonium phosphate pH 7.5 |
| Buffer A | 3% (v/v) acetonitrile, aqueous ammonium phosphate, pH 7.5 |
| Buffer B | 67% (v/v) acetonitrile, aqueous ammonium phosphate, pH 7.5 |

| Elution protocol | | | | |
|---|---|---|---|---|
| Time [min] | Flow rate [ml/min] | Buffer A [%] | Buffer B [%] | Remarks |
| 0 | 90 | 100 | 0 | Flushing |
| 20 | 90 | 100 | 0 | post loading |
| 21 | 90 | 76 | 24 | Elution |
| 103 | 90 | 0 | 100 | linear gradient |

The pooled fractions obtained from the first RP-HPLC step were further purified as set forth in Table 4.

TABLE 4

Parameters second purification dimension

| Sample loading buffer | 3% (v/v) acetonitrile, aqueous ammonium phosphate pH 7.5 |
|---|---|
| Buffer A | 3% (v/v) acetonitrile, 0.1% (v/v) aqueous TFA |
| Buffer B | 0.1% (v/v) TFA in acetonitrile |

Elution protocol

| Time [min] | Flow rate [ml/min] | Buffer A [%] | Buffer B [%] | Remarks |
|---|---|---|---|---|
| 0 | 90 | 100 | 0 | Flushing |
| 30 | 90 | 100 | 0 | post loading |
| 31 | 90 | 70 | 30 | Elution: |
| 146 | 90 | 0 | 100 | linear gradient |

The purity of the pooled fractions was after the second purification dimension was 98.8% as assessed by analytical RP-UHPLC, the overall yield after both steps was 35%. Comparison of the analytical RP-UHPLC traces of starting crude material and of the pooled fractions after the first and second HPLC pass demonstrated the surprising complementarity of both purification dimensions: Each purification dimension removed different unwanted components, such that the combination of both steps resulted in excellent product purity (cf. FIG. 2).

Example 3: Two Dimensional RP-HPLC Purification

The purification involved a chromatographic purification at pH 7.7 in the first dimension, followed by a chromatographic purification under acidic conditions in the second dimension.

A 5 cm MODcol column (Grace) packed with C8-bonded silica (approx. bed-depth 32 cm) was used on a preparative HPLC system (Knauer HPLC pump 1800) with detection at 220 nm (Knauer smartline UV detector 2500) and an automated fraction collector (Büchi C-660). The same stationary phase was used in both dimensions of the purification protocol. Crude Liraglutide produced by Fmoc SPPS was used as a starting material. The sample was loaded on the column at a flow rate of 43 ml/min (1$^{st}$ dimension) or 64 ml/min (2$^{nd}$ dimension). The detailed elution protocols for each step are given in Tables 5 and 6 below.

TABLE 5

Parameters first purification dimension

| Sample loading buffer | aqueous ammonium phosphate pH 7.7 |
|---|---|
| Buffer A | 3% (m/m) acetonitrile, aqueous ammonium phosphate pH 7.7 |
| Buffer B | 61% (m/m) acetonitrile, aqueous ammonium phosphate pH 7.7 |

Elution protocol

| Time [min] | Flow rate [ml/min] | Buffer A [%] | Buffer B [%] | Remarks |
|---|---|---|---|---|
| 0 | 90 | 100 | 0 | Flushing |
| 20 | 90 | 100 | 0 | post loading |
| 20.1 | 36.5 | 76 | 24 | Elution: |
| 102 | 36.5 | 0 | 100 | linear gradient |

The pooled main fraction obtained from the first RP-HPLC step was further purified as set forth in Table 6.

TABLE 6

Parameters second purification dimension

| Sample loading buffer | 2% (m/m) acetonitrile, aqueous ammonium phosphate pH 7.7 |
|---|---|
| Buffer A | 2% (m/m) acetonitrile, 0.1% (v/v) aqueous TFA |
| Buffer B | 0.1% (v/v) TFA in 100% acetonitrile |

Elution protocol

| Time [min] | Flow rate [ml/min] | Buffer A [%] | Buffer B [%] | Remarks |
|---|---|---|---|---|
| 0 | 90 | 100 | 0 | Flushing |
| 30 | 90 | 100 | 0 | post-loading |
| 30.1 | 36 | 70 | 30 | Elution: |
| 145 | 36 | 0 | 100 | Linear gradient |

The purity of the pooled main fraction was 99.38%, and the largest non-product peak was 0.18% as assessed by analytical RP-UHPLC. In other words, the preparation did not contain any unwanted component at a concentration above 0.3 as assessed by analytical RP-UHPLC.

Surprisingly, an attempt to swap the order of purification steps, i.e. to perform the run with the TFA-containing mobile phase first, failed due to column clogging.

Example 4: RP-HPLC Purification, Optional 3rd Dimension

A 5 cm MODcol column (Grace) packed with C8-bonded silica (approx. bed-depth 32 cm) was used on a preparative HPLC system (Knauer HPLC pump 1800) with detection at 220 nm (Knauer smartline UV detector 2500) and an automated fraction collector (Büchi C-660). Liraglutide purified by the two-dimensional approach given above was used as a starting material (purity: 99.2%). The column was equilibrated in Buffer A and the sample was loaded on the column at a flow rate of 43 ml/min. The detailed elution protocol is given in Table 7 below.

The purity of the pooled main fraction was 99.35% as assessed by analytical RP-UHPLC with UV detection at 220 nm. The preparation did not contain any peptidic impurity at a concentration above 0.3%.

TABLE 7

Parameters third purification dimension

| Sample loading buffer | 3% (m/m) acetonitrile, aqueous sodium hydrogen phosphate, pH 7.7 |
|---|---|
| Buffer A | 3% (m/m) acetonitrile, aqueous sodium hydrogen phosphate, pH 7.7 |
| Buffer B | 61% (m/m) acetonitrile, aqueous sodium hydrogen phosphate, pH 7.7 |

Elution protocol

| Time [min] | Flow rate [ml/min] | Buffer A [%] | Buffer B [%] | Remarks |
|---|---|---|---|---|
| 0 | 89 | 100 | 0 | Flushing |
| 20 | 89 | 100 | 0 | post loading |
| 20.1 | 36.5 | 76 | 24 | Elution: |
| 102 | 36.5 | 0 | 100 | Linear gradient |

Example 5: RP-HPLC Purification, Optional 3rd Dimension

A 5 cm MODcol column (Grace) packed with C8-bonded silica (approx. bed-depth 32 cm) was used on a preparative HPLC system (Knaur HPLC pump 1800) with detection at 220 nm (Knaur smartline UV detector 2500) and an automated fraction collector (Büchi C-660). Liraglutide purified by the two-dimensional approach given above was used as a starting material. The column was equilibrated in Buffer A and the sample was loaded on the column at a flow rate of 43 ml/min. The detailed elution protocol is given in Table 8 below.

TABLE 8

Parameters third purification dimension

| | |
|---|---|
| Sample loading buffer | 3% (m/m) acetonitrile, aqueous disodium hydrogen phosphate, pH 7.5 |
| Buffer A | 3% (m/m) acetonitrile, aqueous disodium hydrogen phosphate, pH 7.5 |
| Buffer B | 61% (m/m) acetonitrile, aqueous disodium hydrogen phosphate, pH 7.5 |

Elution protocol

| Time [min] | Flow rate [ml/min] | Buffer A [%] | Buffer B [%] | Remarks |
|---|---|---|---|---|
| 0 | 89 | 100 | 0 | Flushing |
| 20 | 89 | 100 | 0 | post loading |
| 20.1 | 36.5 | 76 | 24 | Elution: |
| 102 | 36.5 | 0 | 100 | Linear gradient |

The purity of the pooled main fraction was 99.36% as assessed by analytical RP-UHPLC. The preparation did not contain any peptidic impurity at a concentration above 0.3%.

Example 6: Desalting by Ultrafiltration

UHPLC purified Liraglutide (1.7 l, concentration approximately 35 g/l) was subjected to tangential flow filtration using standard equipment with a polyethersulfone (PES) membrane having a molecular weight cut-off of 1 kDa. A transmembrane pressure of 2.2 bar and a flow rate of 1 l/min were applied, and a permeate flow of 33 ml/min was observed. The volume loss in the retentate was compensated by constant addition of ultrapure water.

Figure 3:
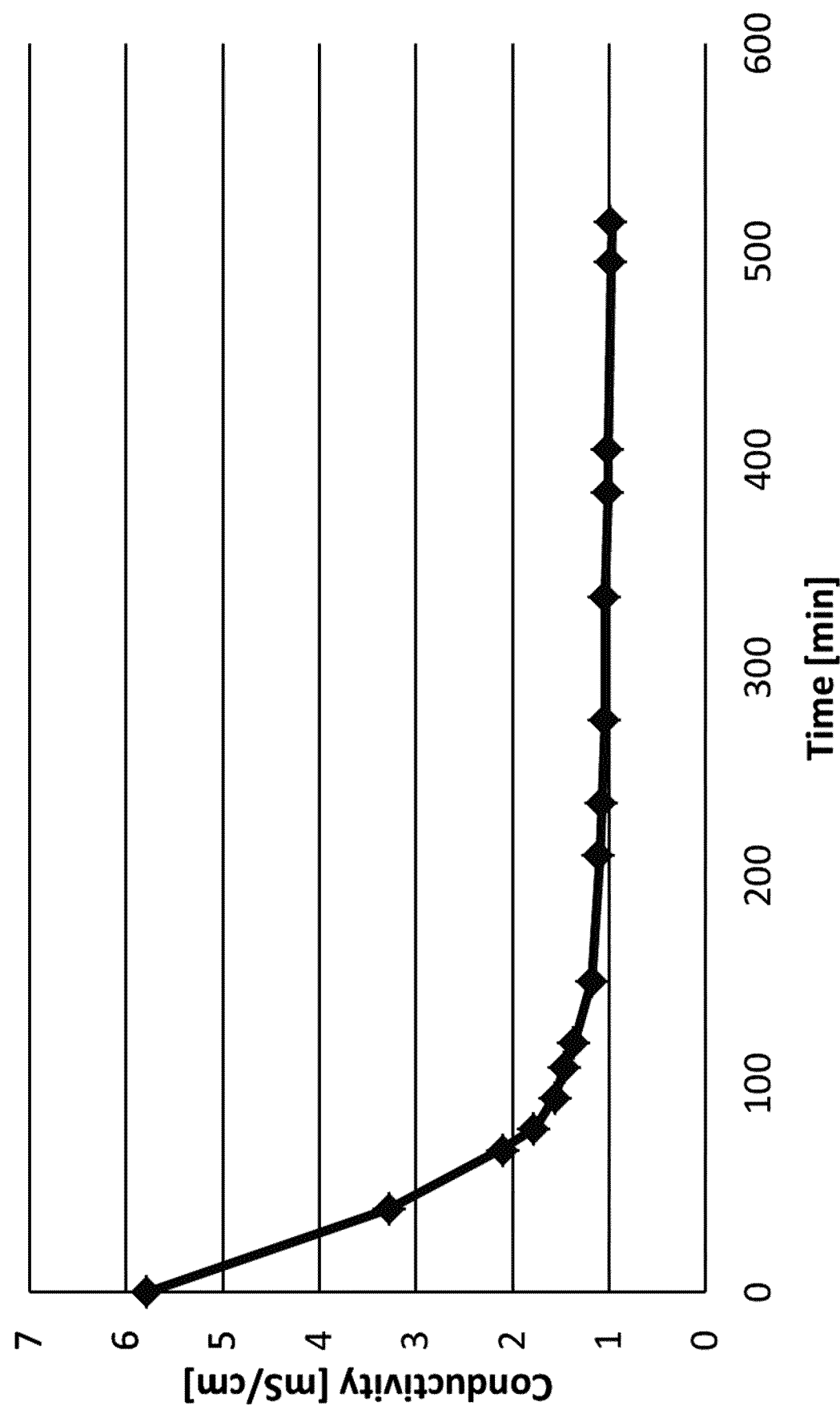
FIG. 3: Plot of Conductivity of the retentate versus time during ultrafiltration.

As shown in FIG. 3, the salt content as reflected by the retentate's conductivity decreased over time. When the volume of the filtrate reached 10 fold the volume of the retentate, the retentate contained only traces of residual salt. The peptide purity as detected by UHPLC analysis was 99.3, the overall net peptide yield was 91%.

Example 7: Removal of Unwanted Components During Purification

Liraglutide obtained from Fmoc-SPPS was subjected to the three-dimensional purification method of the present invention. C8-bonded silica was employed as stationary phase, and the aqueous component of the mobile phase contained phosphate buffer in the first dimension, TFA in the second dimension and acetate buffer in the third dimension. The pooled fractions obtained after each step were analyzed by LC-MS to evaluate the efficiency of the purification protocol. The findings relating to specific dominant unwanted components are summarized in Table 9 below. The concentrations are given in area percent of the Liraglutide main peak.

It can be seen that the Liraglutide truncation variant lacking $Gly^{31}$ and Liraglutide with mono-oxygenated $Trp^{25}$ are efficiently reduced by the first purification dimension, the second purification dimension achieves additional removal of Liraglutide with di-oxygenated $Trp^{25}$ and the third purification dimension achieves control of $Kyn^{25}$-Liraglutide. No other peptidic impurity was detectable at levels above 0.5% by analytic chromatography in the pooled fractions after the $3^{rd}$ purification dimension.

TABLE 9

| | Sample | | | |
|---|---|---|---|---|
| | Des-$Gly^{31}$-Liraglutide | $Trp(O)^{25}$-Liraglutide | $Trp(2O)^{25}$-Liraglutide | $Kyn^{25}$-Liraglutide |
| crude | 0.47 | 2.17 | 0.20 | 0.85 |
| Pool after $1^{st}$ dimension | <0.01 | 0.33 | 0.05 | 0.33 |
| Pool after $2^{nd}$ dimension | not detected | 0.04 | 0.02 | 0.34 |
| Pool after $3^{rd}$ dimension | not detected | 0.02 | 0.01 | 0.01 |

---

The invention claimed is:

1. A method for the purification of Liraglutide, comprising:
   a) providing a liquid composition C comprising crude Liraglutide and at least one unwanted component;
   b) subjecting the composition C to a first reversed phase high performance liquid chromatograph (RP-HPLC) purification at a pH between 7.0 and 7.8, wherein a hydrocarbon bonded silica is used as a stationary phase, a mobile phase comprising an aqueous phosphate buffer AB1 and acetonitrile is used, and elution is effected by gradually increasing the acetonitrile concentration within the mobile phase while collecting Liraglutide containing fractions; and
   c) subjecting the pooled Liraglutide containing fractions obtained in step b) to a second reversed phase HPLC purification at a pH below 3.0, wherein a hydrocarbon bonded silica is used as a stationary phase, a mobile phase comprising trifluoroacetic acid and acetonitrile is used, and elution is effected by gradually increasing the acetonitrile concentration within the mobile phase while collecting fractions containing purified Liraglutide.

2. The method according to claim 1, wherein the aqueous phosphate buffer AB1 in step b) is ammonium phosphate buffer.

3. The method according to claim 1, wherein the gradient in step b) is selected from the range of 19 to 67% (v/v) acetonitrile and/or wherein the gradient in step c) is selected from the range of 31 to 100% (v/v) acetonitrile.

4. The method according to claim 1, wherein the trifluoroacetic acid concentration within the mobile phase used in step c) is selected from the range of 0.05 to 0.5% (v/v).

5. The method according to claim 1, further comprising the step of:
   d) subjecting the Liraglutide obtained in step c) to a third reversed phase HPLC purification at a pH between 7.0 and 7.8, wherein a hydrocarbon bonded silica is used as a stationary phase, a mixture of an aqueous buffer AB2 with acetonitrile is used as a mobile phase, and elution is effected by gradually increasing the acetonitrile concentration within the mobile phase while collecting fractions containing purified Liraglutide.

6. The method according to claim 5, wherein said aqueous buffer AB2 is selected from the group consisting of:
   a mixture of sodium dihydrogen phosphate and disodium hydrogen phosphate,
   a mixture of potassium dihydrogen phosphate and dipotassium hydrogen phosphate,
   potassium acetate, and
   sodium acetate.

7. The method according to claim 1, wherein all or parts of step b) and/or step c) and/or step d), if present, is/are carried out at a temperature selected from the range of 4° C. to 25° C.

8. The method according to claim 1, wherein the stationary phase used in steps b) and c) and step d), if present, is C8 bonded silica or C18 bonded silica.

9. The method according to claim 1, further comprising a step e) of size exclusion chromatography.

10. The method according to claim 1, further comprising a step f) of desalting the peptide.

11. The method according to claim 9, wherein all or parts of the respective step is/are carried out at a temperature selected from the range of 4° C. to 20° C.

12. The method according to claim 1, wherein step a) comprises dissolving a dried crude Liraglutide peptide in an aqueous phosphate buffer AB0 at a pH selected from the range of 7.0 to 7.5.

13. The method according to claim 1, wherein the crude Liraglutide peptide is obtained by solid phase peptide synthesis, followed by trifluoroacetic acid mediated cleavage and peptide precipitation from the cleavage composition.

14. The method according to claim 1, wherein a purified Liraglutide is lyophilized.

15. The method according to claim 2, wherein the aqueous phosphate buffer AB1 in step b) is ammonium phosphate buffer at a concentration of 5 mM to 50 mM.

16. The method according to claim 4, wherein the trifluoroacetic acid concentration within the mobile phase used in step c) is selected from the range of 0.05 to 0.1% (v/v).

17. The method according to claim 7, wherein all or parts of step b) and/or step c) and/or step d), if present, is/are carried out at a temperature selected from the range of 4° C. to 10° C.

18. The method according to claim 10, wherein the desalting the peptide is performed by ion exchange chromatography, by size exclusion chromatography, or by ultrafiltration.

19. The method according to claim 11, wherein all or parts of the respective step is/are carried out at a temperature selected from the range of 4° C. to 10° C.

20. The method according to claim 14, wherein a purified Liraglutide is lyophilized at a pH selected from the range of 6.6 to 7.9.

* * * * *

SEQUENCE LISTING

<160> NUMBER OF SEQ ID NOS: 7

<210> SEQ ID NO 1
<211> LENGTH: 28
<212> TYPE: PRT
<213> ORGANISM: Homo sapiens

<400> SEQUENCE: 1

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn
            20                  25

<210> SEQ ID NO 2
<211> LENGTH: 33
<212> TYPE: PRT
<213> ORGANISM: Homo sapiens

```
<400> SEQUENCE: 2

His Ala Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
                20                  25                  30

Asp

<210> SEQ ID NO 3
<211> LENGTH: 31
<212> TYPE: PRT
<213> ORGANISM: Homo sapiens

<400> SEQUENCE: 3

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
                20                  25                  30

<210> SEQ ID NO 4
<211> LENGTH: 31
<212> TYPE: PRT
<213> ORGANISM: Artificial Sequence
<220> FEATURE:
<223> OTHER INFORMATION: glucagon-like peptide liraglutide polypeptide

<400> SEQUENCE: 4

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
                20                  25                  30

<210> SEQ ID NO 5
<211> LENGTH: 39
<212> TYPE: PRT
<213> ORGANISM: Homo sapiens

<400> SEQUENCE: 5

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
                20                  25                  30

Ser Gly Ala Pro Pro Pro Ser
        35

<210> SEQ ID NO 6
<211> LENGTH: 39
<212> TYPE: PRT
<213> ORGANISM: Artificial Sequence
<220> FEATURE:
<223> OTHER INFORMATION: glucagon-like peptide exenatide

<400> SEQUENCE: 6

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
                20                  25                  30

Ser Gly Ala Pro Pro Pro Ser
        35

<210> SEQ ID NO 7
<211> LENGTH: 44
```

```
<212> TYPE: PRT
<213> ORGANISM: Artificial Sequence
<220> FEATURE:
<223> OTHER INFORMATION: glucagon-like peptide lixisenatide

<400> SEQUENCE: 7

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Lys Lys Lys Lys Lys Lys
        35                  40
```